United States Patent
Arendash

(10) Patent No.: US 11,911,629 B2
(45) Date of Patent: Feb. 27, 2024

(54) TREATMENT OF PRIMARY AND METASTATIC BRAIN CANCERS BY TRANSCRANIAL ELECTROMAGNETIC TREATMENT

(71) Applicant: NeuroEM Therapeutics, Inc., Phoenix, AZ (US)

(72) Inventor: Gary W. Arendash, Phoenix, AZ (US)

(73) Assignee: NeurEM Therapeutics, Inc., Tampa Bay, FL (US)

( * ) Notice: Subject to any disclaimer, the term of this patent is extended or adjusted under 35 U.S.C. 154(b) by 0 days.

(21) Appl. No.: 17/538,889

(22) Filed: Nov. 30, 2021

(65) Prior Publication Data
US 2022/0111224 A1    Apr. 14, 2022

Related U.S. Application Data

(63) Continuation-in-part of application No. 16/359,749, filed on Mar. 20, 2019, and a continuation-in-part of
(Continued)

(51) Int. Cl.
*A61N 2/02* (2006.01)
*A61N 2/00* (2006.01)
(Continued)

(52) U.S. Cl.
CPC ............ *A61N 1/40* (2013.01); *A61N 1/0476* (2013.01); *A61N 1/36025* (2013.01); *A61N 2/004* (2013.01); *A61N 2/02* (2013.01)

(58) Field of Classification Search
CPC .... A61N 1/0476; A61N 1/36025; A61N 1/40; A61N 2/004; A61N 2/02; A61N 5/022
(Continued)

(56) References Cited

U.S. PATENT DOCUMENTS 6,248,126 B1    6/2001  Lesser
6,334,069 B1   12/2001  George
(Continued)

FOREIGN PATENT DOCUMENTS

EP    1907052        1/2010
EP    1606010 B1     2/2012
(Continued)

OTHER PUBLICATIONS

Arendash; "Transcranial Electromagnetic Treatment Against Alzheimer's Disease: Why it has the Potential to Trump Alzheimer's Disease Drug Development," Journal of Alzheimer's Disease, 32 (Jun. 2012) pp. 243-266.
(Continued)

*Primary Examiner* — Carl H Layno
*Assistant Examiner* — Jane C Kalinock
(74) *Attorney, Agent, or Firm* — Nathan G. Guymon, Esq.; Bamert Regan PLLC

(57) ABSTRACT

There is a present unmet need for non-invasive therapeutic methods for administration to brain cancer subjects that would provide a robust attack against their primary or metastatic brain cancer. The present disclosure describes such methods to therapeutically induce regression and/or elimination of primary and metastatic brain cancers through Transcranial Electromagnetic Treatment (TEMT). The methods involve 1) enhancement of brain meningeal lymph flow to increase immune trafficking between the brain cancer and cervical lymph nodes, 2) rebalancing of immune or non-immune signaling within the brain, particularly from the brain tumor to the lymphatic system, and/or 3) direct attack on cells within and around the brain tumor itself. Thus, the above described TEMT methods could induce and boost a specific immune or non-immune response to a given brain tumor, as well as directly attack the brain tumor, to
(Continued)

provide an effective therapeutic intervention against both primary and metastatic brain cancers.

21 Claims, 18 Drawing Sheets

Related U.S. Application Data application No. 16/273,519, filed on Feb. 12, 2019, now Pat. No. 11,752,356, and a continuation-in-part of application No. 16/865,250, filed on May 1, 2020, now Pat. No. 11,759,650, which is a continuation-in-part of application No. 14/205,333, filed on Mar. 11, 2014, now Pat. No. 10,765,879, application No. 17/538,889 is a continuation-in-part of application No. 17/508,727, filed on Oct. 22, 2021.

(60) Provisional application No. 61/776,097, filed on Mar. 11, 2013.

(51) Int. Cl.
  *A61N 1/40* (2006.01)
  *A61N 1/36* (2006.01)
  *A61N 1/04* (2006.01)

(58) Field of Classification Search
  USPC .......................................................... 607/154
  See application file for complete search history.

(56) References Cited

U.S. PATENT DOCUMENTS

| | | |
|---|---|---|
| 6,410,137 B1 | 6/2002 | Bunyan |
| 6,463,336 B1 | 10/2002 | Mawhinney |
| 6,876,337 B2 | 4/2005 | Larry |
| 7,672,648 B1 | 3/2010 | Groe |
| 8,684,901 B1 | 4/2014 | Zabara |
| 8,868,177 B2 | 10/2014 | Simon et al. |
| 9,672,393 B1 | 6/2017 | Zhu |
| 10,792,483 B2 | 10/2020 | Andocs |
| 10,850,096 B2 | 12/2020 | Teng |
| 11,058,886 B1 | 7/2021 | Matloubian |
| 11,229,788 B1 | 1/2022 | John |
| 2004/0122281 A1 | 6/2004 | Fischell |
| 2004/0127895 A1 | 7/2004 | Flock |
| 2004/0176805 A1 | 9/2004 | Whelan |
| 2004/0181115 A1 | 9/2004 | Sandyk |
| 2004/0199070 A1 | 10/2004 | Krockel |
| 2005/0228209 A1 | 10/2005 | Schneider |
| 2007/0244530 A1 | 10/2007 | Ren |
| 2008/0269851 A1 | 10/2008 | Deem |
| 2009/0131739 A1 | 5/2009 | Shalev |
| 2009/0156884 A1 | 6/2009 | Schneider |
| 2009/0276019 A1 | 11/2009 | Perez |
| 2010/0042168 A1 | 2/2010 | Pasche |
| 2010/0114086 A1 | 5/2010 | Deem |
| 2010/0210894 A1 | 8/2010 | Pascual-Leone |
| 2011/0230701 A1 | 9/2011 | Simon |
| 2012/0065456 A1 | 3/2012 | Arendash |
| 2012/0089201 A1 | 4/2012 | Pilla |
| 2012/0172954 A1 | 7/2012 | Zastrow |
| 2012/0289869 A1 | 11/2012 | Tyler |
| 2013/0237742 A1 | 9/2013 | Capstick |
| 2014/0187851 A1 | 7/2014 | Cetroni |
| 2014/0228620 A1 | 8/2014 | Vasishta |
| 2014/0303425 A1* | 10/2014 | Pilla ........................ A61B 6/037 600/15 |
| 2014/0330353 A1 | 11/2014 | Knight |
| 2015/0057736 A1* | 2/2015 | Zachar ...................... A61N 5/04 607/154 |
| 2015/0209566 A1* | 7/2015 | Peyman ............... A61B 5/0036 604/20 |
| 2015/0342661 A1 | 12/2015 | Ron Edoute |
| 2016/0022976 A1 | 1/2016 | Peyman |
| 2016/0106997 A1* | 4/2016 | Arendash ............... A61N 2/006 600/13 |
| 2017/0014637 A1 | 1/2017 | Basser |
| 2017/0065326 A1 | 3/2017 | Rosen |
| 2017/0209579 A1 | 7/2017 | Curley |
| 2019/0030354 A1 | 1/2019 | Turner |
| 2019/0290355 A1 | 9/2019 | Amos |
| 2020/0038509 A1 | 2/2020 | Corr |
| 2020/0078600 A1 | 3/2020 | Dinh |
| 2020/0164195 A1 | 5/2020 | Lowsky |
| 2020/0297286 A1 | 9/2020 | Costa |
| 2020/0346028 A1 | 11/2020 | Neuroem |
| 2021/0153925 A1 | 5/2021 | Kim |
| 2021/0177491 A1 | 6/2021 | Onik |
| 2021/0220480 A1 | 7/2021 | Peyman |
| 2021/0338265 A1 | 11/2021 | Cohn |
| 2022/0054856 A1* | 2/2022 | Wang .................. A61N 1/36025 |

FOREIGN PATENT DOCUMENTS

| | | |
|---|---|---|
| EP | 2414038 | 8/2012 |
| WO | 2007044386 | 4/2007 |
| WO | 2008008545 | 9/2008 |
| WO | 2008141296 | 11/2008 |
| WO | 2017157874 | 9/2017 |
| WO | 2020102312 A1 | 5/2020 |
| WO | 2020141527 | 7/2020 |
| WO | 2020180653 | 9/2020 |

OTHER PUBLICATIONS

Nguyen, et al; "The Effect of a High Frequency Electromagnetic Field in the Microwave Range on Red Blood Cells"; Sep. 7, 2017.
Karsten, et al; "Red Blood Cells are Dynamic Reservoirs of Cytokines"; Feb. 15, 2018.
Arendash; A Clinical Trial of Transcranial Electromagnetic Treatment in Alzheimer's Disease: Cognitive Enhancement and Associated Changes in Cerebrospinal Fluid, Blood, and Brain Imaging; Journal of Alzheimer's Disease 71 (2019) pp. 57-82.
Arendash; Review of the Evidence that Transcranial Electromagnetic Will Be a Safe and Effective Therapeutic Against Alzheimer's Disease; Journal of Alzheimer's Disease 53 (2016) pp. 753-771.
Rasouli; "Attenuation of interleukin-1beta by pulsed electromagnetic fields after traumatic brain injury"; Neuroscience Letters 519 (2012) 4-8.
Merighi; "Signaling pathways involved in anti-inflammatory effects of Pulsed Electromagnetic Field in microglial cells"; Cytokine 125 (2020) 154777.
Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.
Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.
Gerstner Elizabeth R. et al., AntiEndothelial Growth Factor Therapy for Malignant Glioma, Curr Neurol Neurosci Rep. May 2009, 9(3):254-262, p. 2, paragraphs 2-3.
Gerstner Elizabeth R. et al., AntiEndolhelial Growth Factor Therapy for Malignant Glioma, Curr Neurol Neurosci Rep. May 2009, 9(3):254-262, p. 2, paragraphs 2-3.

* cited by examiner

*p<0.05, p<0.02, or *p<0.001 compared to "Lower BL Levels" for that cytokine/immune mediator

TREATMENT OF PRIMARY AND METASTATIC BRAIN CANCERS BY TRANSCRANIAL ELECTROMAGNETIC TREATMENT

RELATED APPLICATIONS

The present application claims benefit to and is a continuation-in-part of U.S. application Ser. No. 16/865,250 now U.S. Pat. No. 11,759,650, filed May 1, 2020, which is a continuation-in-part of U.S. application Ser. No. 14/205,333, filed Mar. 11, 2014, which claims the benefit of U.S. Provisional Application No. 61/776,097, filed Mar. 11, 2013. The present application also claims benefit to and is a continuation-in-part of U.S. application Ser. No. 16/273,519 now U.S. Pat. No. 11,752,356, filed Feb. 12, 2019. The present application also claims benefit to and is a continuation-in-part of U.S. application Ser. No. 16/359,749, filed Mar. 20, 2019. The present application also claims benefit to and is a continuation-in-part of U.S. application Ser. No. 17/508,727, filed Oct. 22, 2021. These applications are incorporated herein by reference in their entireties.

BACKGROUND OF INVENTION

Brain tumors, including primary and metastatic tumors, are among the most feared and deadly forms of cancer, having few treatment options and a poor prognosis. Although primary brain tumors include Chordomas, Ependymomas, Schwannomas, and pituitary tumors, the most prevalent are glial cell cancers (called "gliomas") such as glioblastomas, astrocytomas, oligodendrogliomas, and oligoastrocytomas. Collectively, gliomas are responsible for around 75% of all primary brain cancers. Cerebral gliomas such as glioblastomas have a strong propensity to spread to other brain areas. Nonetheless, metastatic brain cancers spreading to the brain from other locations in the body remain the most frequently-occurring brain cancers.

Therapeutic approaches to slow or arrest primary or metastatic brain cancers have thus far failed, with a survival time after glioma diagnosis being around 1 to 1½ years depending on whether a low- or high-grade cancer is present. Some of the few treatment options for brain cancer patients are radiation therapy, chemotherapy, and/or gamma knife radiosurgery, none of which add substantially to survival or quality of life. A relatively new approach specifically for brain gliobastomas is the use of Tumor Treating Fields (TTFs), which are electric fields generated by electrical current running through a gridded mat placed on the bald head of patients for 18 hours a day. TTFs, which appear to act by impeding division of cancer cells, add only a few months to survival of gliobastoma patients. Thus, there is no therapeutic intervention currently known to affect this lethal primary brain tumor type.

New experimental treatments against cancers in general are presently being explored, but are largely pre-clinical or at proof-of-concept stages at the present time—moreover, they are invasive and/or not practical for cancers in the brain. In this regard, thermal/heat-based therapeutics are used for ablation of solid cancers outside of the brain. These include radiofrequency (RF) thermal, microwave, and high intensity focused ultrasound ablation—all of which raise tissue temperature 45° C. or higher for general ablation of cancerous tissues. For example, RF thermal ablation induce vibrations in the cell membrane that are converted to heat by friction. Cell death occurs in as little as 30 second once the cell temperature reaches 50° C. Such thermal-based RF approaches to solid cancer treatment suffer from the drawback that they have little or no ability to spare normal structures in the treatment zone (non-specific). This would be an unacceptable risk for brain tumors, likely leading to serious complications from collateral normal brain tissue damage. Other approaches against cancer in general use RF (thermal or non-thermal) treatment as only one of several therapeutic components, most commonly in combination with drug/agent administration (e.g., systemic administration of an immune stimulant before or after RF treatment). All RF-based therapeutic interventions against cancer in general employ low frequencies (below 50 MHz), and many would be invasive and/or ineffective against primary or metastatic brain cancers, in part because the cranium would present a significant barrier.

Other approaches against cancers in general are purely immune-based. For example, in "dendritic cell immunotherapy" the patient's immature immune cells are coaxed into growing into dendritic cells, which may then boost the immune system's attack on a given brain cancer. Once these cells have been produced, they are modified to train the patient's own immune T-cells to attack certain proteins, or antigens, on the surface of the tumor cells in the brain that are not on the surface of normal cells.

Ideally, the body's immune system would be called in to attack, kill, and/or contain brain cancer cells. Unfortunately, the immune response to the presence of brain cancers such as gliomas is minimal and ineffective. This is due, firstly, to a lack of lymphatic vessels within the brain parenchyma through which to transport specific memory T-cells to the glioma. Secondly, the immune response to cancers in the brain is inherently small and insufficient for inducing arrest or regression of brain cancers, most notably gliomas. This later issue is important since, if the immune system could respond more vigorously to the brain tumor, there is reasonable expectation that an arresting of tumor growth or actual brain tumor regression may occur.

Up until recently, it was believed that there were no functional lymphatic vessels in the brain capable of working in concert with the blood's immune system to mount a robust attack on brain cancers; specifically through lymph node production of immune cells and their transport via blood to the brain tumor location. The only connectivity/communication between the brain and blood immune system was thought to be by brain interstitial fluid drainage into the Cerebrospinal Fluid (CSF) and then from CSF into the systemic vascular circulation.

However, new studies have now described a heretofore unknown group of lymphatic vessels in the brain, called meningeal lymphatic vessels (MLVs). MLVs are located parallel to dural venous sinuses and the middle meningeal arteries and are present both dorsally and basally relative to the brain and skull. The "basal" MLVs are primary involved with draining toxins from the brain, while "dorsal" MLVs seem primarily involved with trafficking of immune cells from the brain into cervical lymph nodes, wherein a specific immune response can be generated by specific memory T-cells against a particular brain cancer. These memory T-cells would then travel through the systemic circulation to the brain to provide an immune-based attack on brain cancers. However, this immune-based attack on brain cancers is presently weak and ineffective.

BRIEF DESCRIPTION OF THE DRAWINGS

The accompanying drawings illustrate various examples of the principles described herein and are a part of the specification. The illustrated examples do not limit the scope of the claims.

The presented figures provide examples and/or implementations consistent with the methods described in this provisional application. However, the description is not limited to the examples and/or implementations shown in the figures.

DETAILED DESCRIPTION OF THE INVENTION

A method is needed to provide for a robust, immune cell invasion of brain tumors to stop their growth and induce their regression. Alternatively, or in concert, a method is needed to provide a generalized re-balancing of immune function in the tumor-bearing brain (to make for an inhospitable environment for tumor growth/survival). In addition to a vigorous immune response that attacks brain tumors, a "direct" attack of brain tumor cells (both primary and metastasis-based) by a therapeutic intervention would be highly desirable to directly kill or induce regression of brain tumors through non-immunologic mechanisms. Of particular benefit against brain tumors would be a concerted attack by both direct actions and a strong immune response to a given brain tumor. Thus, it can be concluded that there is not only a need to develop methods to provide a robust immune attack against brain tumors or a rebalancing of the immune system in the brain/tumor, but also a need to directly and effectively attack cells within brain tumors and/or make for an inhospitable environment for their survival.

The present methods provide for a robust specific enhancement of immune responses to brain tumors, a rebalancing of immune markers in and around brain tumors, and a direct attack on brain tumor cells—all through a single, non-invasive and safe medical device that provides transcranial electromagnetic/radiofrequency treatment to the entire forebrain for treatment of multiple brain tumor types (both seen and unseen). As such, these methods represent an entirely new modus operandi to treat all types of brain tumors in a clinical setting and/or in-home and non-invasively, especially primary brain cancers such as gliomas.

Primary and metastatic brain cancers are among the deadliest cancers and essentially mean a death sentence to the subject within a short period. Affected subjects cannot be saved by conventional treatments, which include radiation, chemotherapy, and surgical resection. Unfortunately, there is no current therapeutic intervention that is effective in arresting or inducing regression of these brain cancers, particularly for the 75% of primary brain cancers that involve gliomas.

Although it is a principal job of the body's immune system to target and specifically attack brain cancers, the immune system's response to solid "brain" tumors is weak and ineffective. To a considerable degree, this paltry immune response is thought to be due to minimal intra-tumor drainage, which would contain loose tumor cells, memory T-cells, and dendritic cells.

Figure 1:
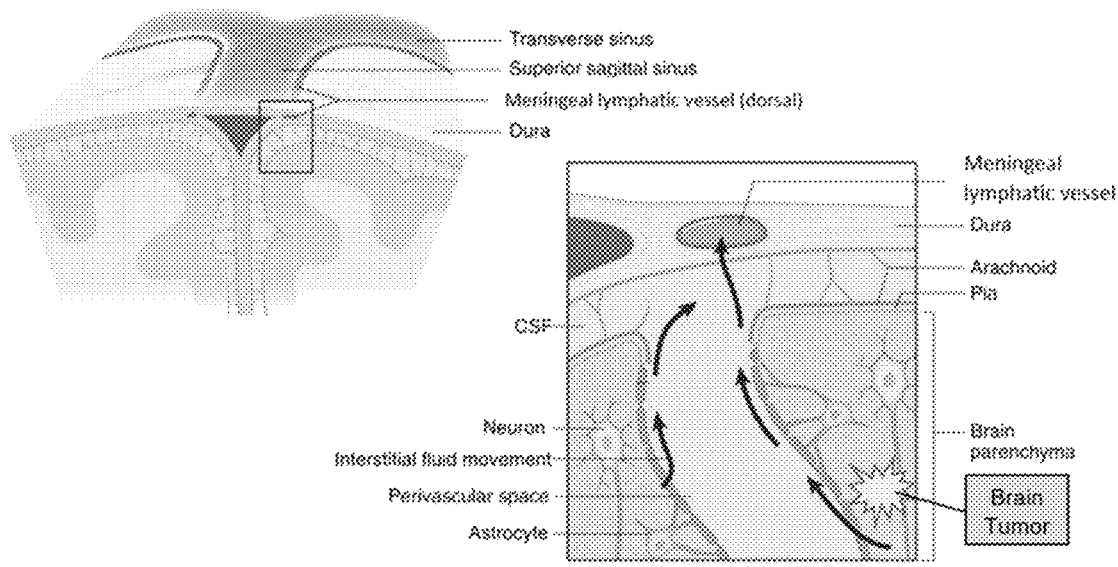
FIG. 1 shows the pathway for intra-tumor drainage, initially going from the interstitial fluid surrounding the tumor to the Cerebrospinal Fluid (CSF), then into meningeal lymphatic vessels for drainage from the brain.
Figure 2:
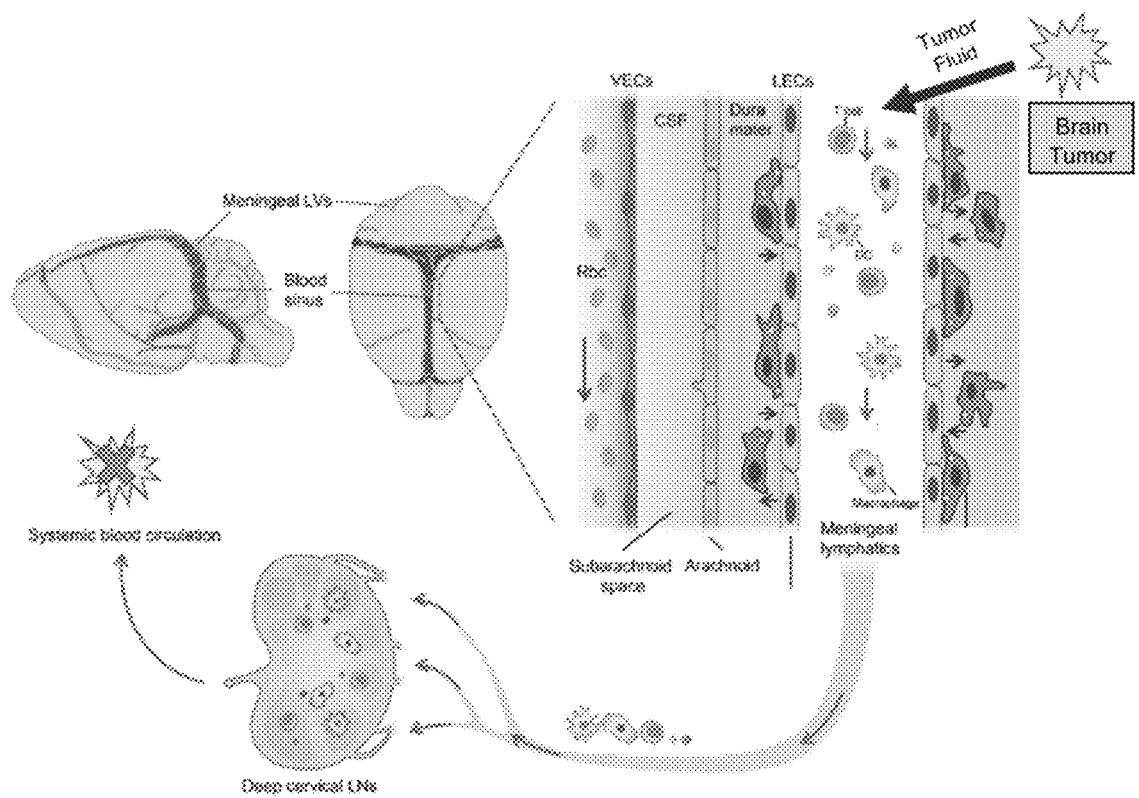
FIG. 2 shows the complete pathway for intra-tumor drainage of memory T-cells and dendritic cells (DC) from the tumor itself in the interstitial fluid into CSF, then into meningeal lymphatic vessels to deep cervical lymph nodes (LNs), with a resultant immune response travelling via the systemic circulation back to the tumor.

Turning now to the figures, FIG. 1 shows the pathway for intra-tumor drainage, initially going from the interstitial fluid surrounding the tumor to the CSF, then into meningeal lymphatic vessels (MLVs). FIG. 2 shows the complete pathway for intra-tumor drainage of memory T-cells and dendritic cells (DC) from the tumor itself in the interstitial fluid into CSF, then into meningeal lymphatic vessels to deep cervical lymph nodes (LNs), with a resultant immune response travelling via the systemic circulation back to the tumor.

Using MLVs as a conduit to cervical lymph nodes, a critical threshold number of memory T-cells/dendritic cells from the brain tumor would then elicit a vigorous and specific immune response of memory T-cells from cervical lymph nodes. These large numbers of memory T-cells would then travel through the systemic circulation to the brain tumor to induce tumor regression/elimination.

Figure 3:
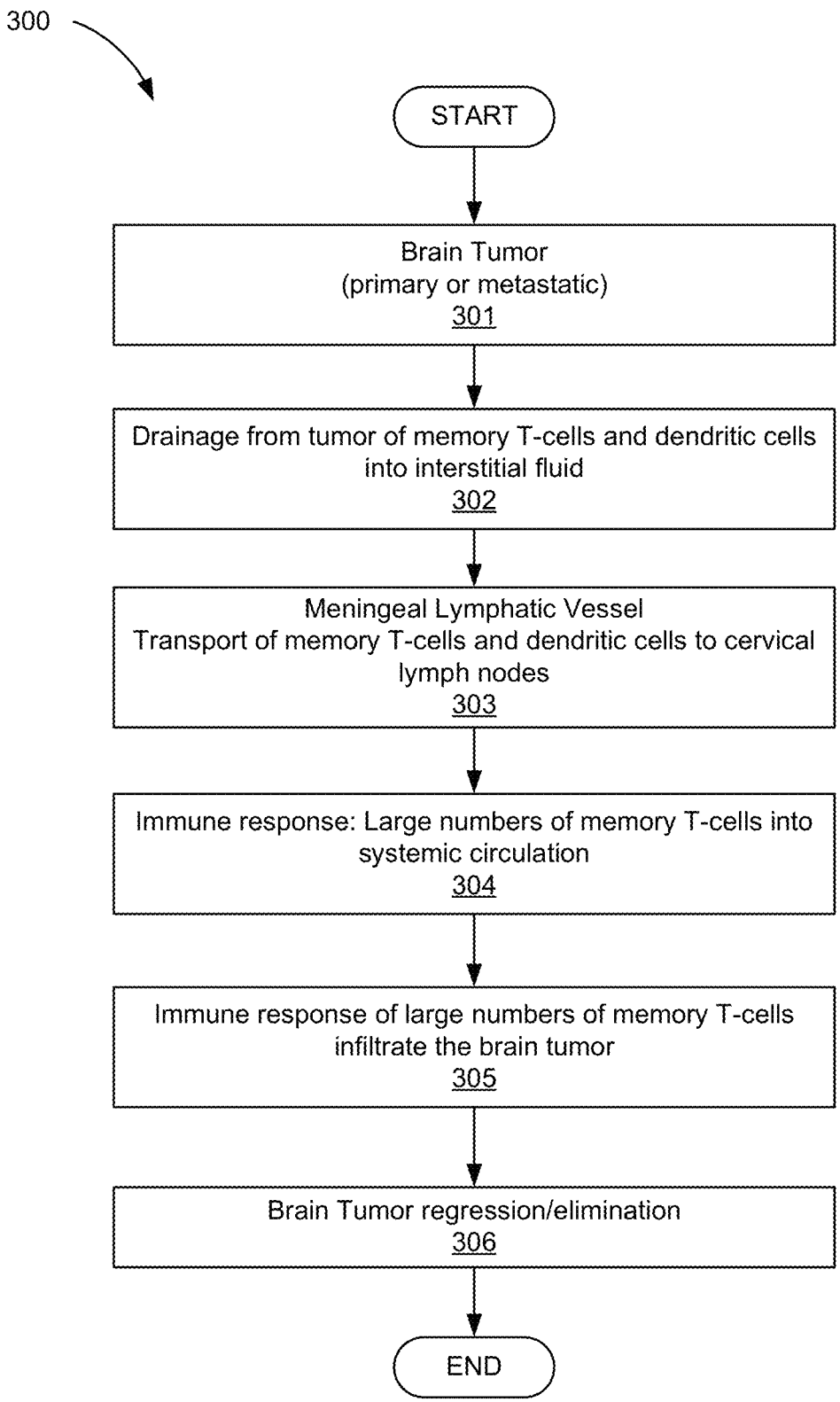
FIG. 3 is a flowchart showing effects of an ideal or increased level of lymph flow through meningeal lymph vessels in the brain (such as may be provided by presently-described methods) and the consequent cascade of events resulting in a strong immune response against brain tumor cells.

FIG. 3 is a flowchart showing an "ideal" immune response involving robust transport of brain tumor drainage through meningeal lymphatic vessels (such as may be provided by the currently-described methods) and the consequent strong immune response elicited from deep cervical lymph nodes against brain tumor cells.

Unfortunately, the small number of memory T-cells that are typically transported from brain tumors to the cervical lymph nodes via MLVs does not induce a significant immune response in those lymph nodes. Therefore, augmentation of MLV function (i.e., lymph vessel dilation) to increase lymph flow from the brain cancer to cervical lymph nodes could be a promising therapeutic intervention for enhancing the communication between brain and immune systems, thus generating a robust, targeted immune-response against a given brain tumor. Unfortunately, the only current method to possibly increase lymph flow through MLVs is to repeatedly inject drugs or immune agents invasively into the brain's CSF via the cisterna magna or into the brain's cerebral ventricles—even this method has thus far only been done in rodents experimentally due to its risk and impracticality.

Thus, there is a present unmet need for non-invasive therapeutic methods for administration to brain cancer subjects that can provide a robust attack against brain tumors either directly or indirectly. These methods could involve 1) an enhancement of MLV lymph flow or MLV restructuring to increase immune trafficking/signaling between the brain cancer and cervical lymph nodes, 2) modulation/rebalancing of immune or non-immune signaling within the brain or specifically from the brain tumor to the lymphatic system, and/or 3) a direct attack on cells within and around the brain tumor itself.

The current specification describes methods to enhance lymph flow/communication through the brain's MLVs or to otherwise modulate/rebalance immune or non-immune signaling in the brain to produce a robust attack on brain cancers, resulting in their regression or atrophy. The current specification also describes methods to directly attack or suppress the activity of cells within the brain tumor itself, including resident microglia/macrophages in and around the brain tumor.

Thus, the above generally-described methods may induce and boost a specific immune or non-immune response to a given brain tumor. The described method may also directly attack any brain tumor to provide the first effective therapeutic intervention against both primary and metastatic brain cancers.

For almost two decades now, negative health effects of electromagnetic waves (particularly radiofrequency waves) have been disparaged by the media and by some in the scientific community, with little supportive real-world evidence. These purported negative health effects have largely involved animals exposed to very high electromagnetic power levels or uncontrolled human epidemiologic (retrospective) studies within a small geographical area in northern Europe. In any event, such claimed negative health effects of electromagnetic fields (particularly radiofrequency fields emitted by cell phones) include an "increased" occurrence of brain cancers (gliomas) induced by cell phone-emitted radiofrequency waves. However, the current specification claims the exact opposite to this still widely-held and erroneous public view that radiofrequency waves emanating from cell phones cause brain cancer. Indeed, the method claims in this specification, backed up by human clinical data, are consistent with Transcranial Electromagnetic Treatment (TEMT) in the radiofrequency range (around 900 MHz) actually causing regression of brain tumors and attainment of complete remission through novel and heretofore unappreciated mechanisms.

By way of background, Transcranial Electromagnetic Treatment (TEMT) is a promising neuromodulatory approach against diseases of aging, such as Alzheimer's Disease (AD). Comprehensive pre-clinical studies in AD transgenic mice have shown that TEMT penetrates the brain and its neurons to "disaggregate" small aggregates/oligomers of two toxic proteins that appear to be the root causes of AD-A$\beta$ and tau. These actions by TEMT, in combination with its ability to enhance mitochondrial function in neurons, appear to play a key role in the consistent cognitive benefits provided by TEMT in AD transgenic mice.

To translate these findings to clinical trials in human AD subjects, the MEMOREM™ device was created to provide full forebrain treatment with radiofrequency waves through multiple emitters distributed on the human head surface. As an example of a device that provides electromagnetic/radiofrequency fields into the brain, the MEMOREM™ device has been shown to provide considerable cognitive benefit to AD subjects, changes in their A$\beta$ levels within cerebrospinal fluid (CSF) consistent with A$\beta$ disaggregation in the brain, and evidence of enhanced brain function in their functional magnetic resonance imaging (fMRI) scans. Thus, interventions such as the MEMOREM™ device that provide electromagnetic field treatment to the human brain provide significant therapeutic benefits against AD. A similar EMF-generating head device for use to treat brain cancers is the OncosEM™, whose use in the various methods of this specification is provided by example.

Accordingly, the present specification provides methods to: 1) elicit a robust immune or non-immune brain response to the presence of a given primary or metastatic brain cancer, and/or 2) directly attack or suppress various cell types within a given primary or metastatic brain cell cancer. Thus, the present specification describes methodologies that can appreciably increase life span and quality of life for subjects bearing brain cancers, perhaps even putting them into permanent remission.

More specifically, methods are provided against brain cancers whereby the human brain is treated with electromagnetic/radiofrequency fields through Transcranial Electromagnetic Treatment (TEMT) to induce beneficial changes in the flow or constituency of lymph traveling through MLVs, or alternatively modulating/rebalancing brain/CSF immune or non-immune mediators. In one example of this method, a TEMT-induced increase in flow through MLVs increases trafficking of memory T-cells/dendritic cells from the brain tumor arriving at cervical lymph nodes. These cervical nodes then induce a vigorous immune response of memory T-cells that then travels via the systemic circulation to the brain tumor to mount a robust attack on the tumor's cells (e.g., as illustrated in FIG. 3). Methods are also provided wherein TEMT "directly" impacts the brain cancer/tumor site to impact the various cell types within a given brain tumor, including microglial cells/macrophages that typically comprise a significant volume of brain tumors. The use of one or more of these bioengineering-based methodologies for brain tumor regression and remission is described in detail within the present specification.

Figure 4:
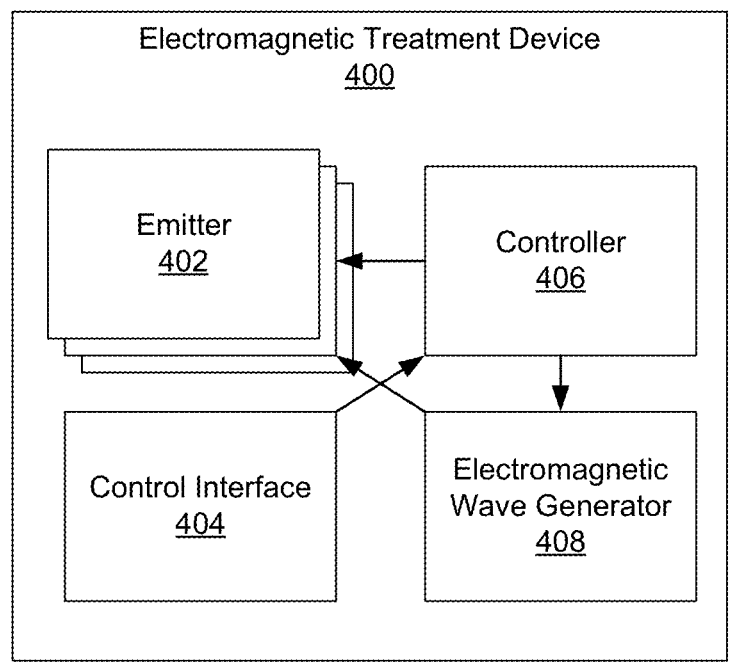
FIG. 4 is a block diagram of an electromagnetic treatment device, according to an example of the principles described herein.

FIG. 4 is a block diagram of an electromagnetic/radiofrequency treatment device (400), according to an example of the principles described herein. Specifically, FIG. 5 depicts an electromagnetic treatment device (400) that includes an array of electromagnetic emitters (402). The electromagnetic emitters (402) may be positioned adjacent a head surface of the subject in, for example, a transcranial electromagnetic treatment (TEMT) device called OncosEM (400). The electromagnetic emitters (402) project an electromagnetic field toward the head of the patient. The electromagnetic emitter(s) (402) is (are) activated to apply electromagnetic fields/treatment to the patient for the remedy of primary or metastatic brain cancers.

In one example, electromagnetic waves may be generated by the electromagnetic wave generator (408), sent to an emitter (402) and then passed into tissue as an electromagnetic field. The electromagnetic treatment device (400) may include a control interface (404), a controller (406), an electromagnetic wave generator (408), and one or more electromagnetic emitters (402) that apply the treatment to the desired portion of the brain/head.

The controller (406) manages the treatment and its parameters by manipulating the electromagnetic wave generator (408) and electromagnetic emitters (402) as per the prescribed treatment. The control interface (404) allows a patient or a care giver to start/stop treatments and to view treatment status. The electromagnetic treatment device (400) may be portable so that treatment can be applied while a patient is moving around at home or could be fixed, allowing a patient to receive treatment when positioned correctly relative to the electromagnetic treatment device (400). Electromagnetic emitters (402) may be activated one at a time by the controller (406), or several electromagnetic emitters (402) may be activated to produce various electromagnetic (e.g., radio frequency) field combinations to produce controllable patterns where desired on the patient.

It should be noted that the TEMT treatment by the electromagnetic treatment device (400) is non-thermal treatment. In some other approaches, RF administration may cause a thermal ablation of the cancer. However, the methods described herein provide for a non-thermal treatment of cancers. In the described methods (unlike RF thermal ablation or cryoablation), the TEMT treatment may kill cancer cells without denaturing the proteins released from the cancer cells. With the released proteins still intact, an even more robust immune response by memory T-cells/dendritic cells may be induced.

Figure 5A:
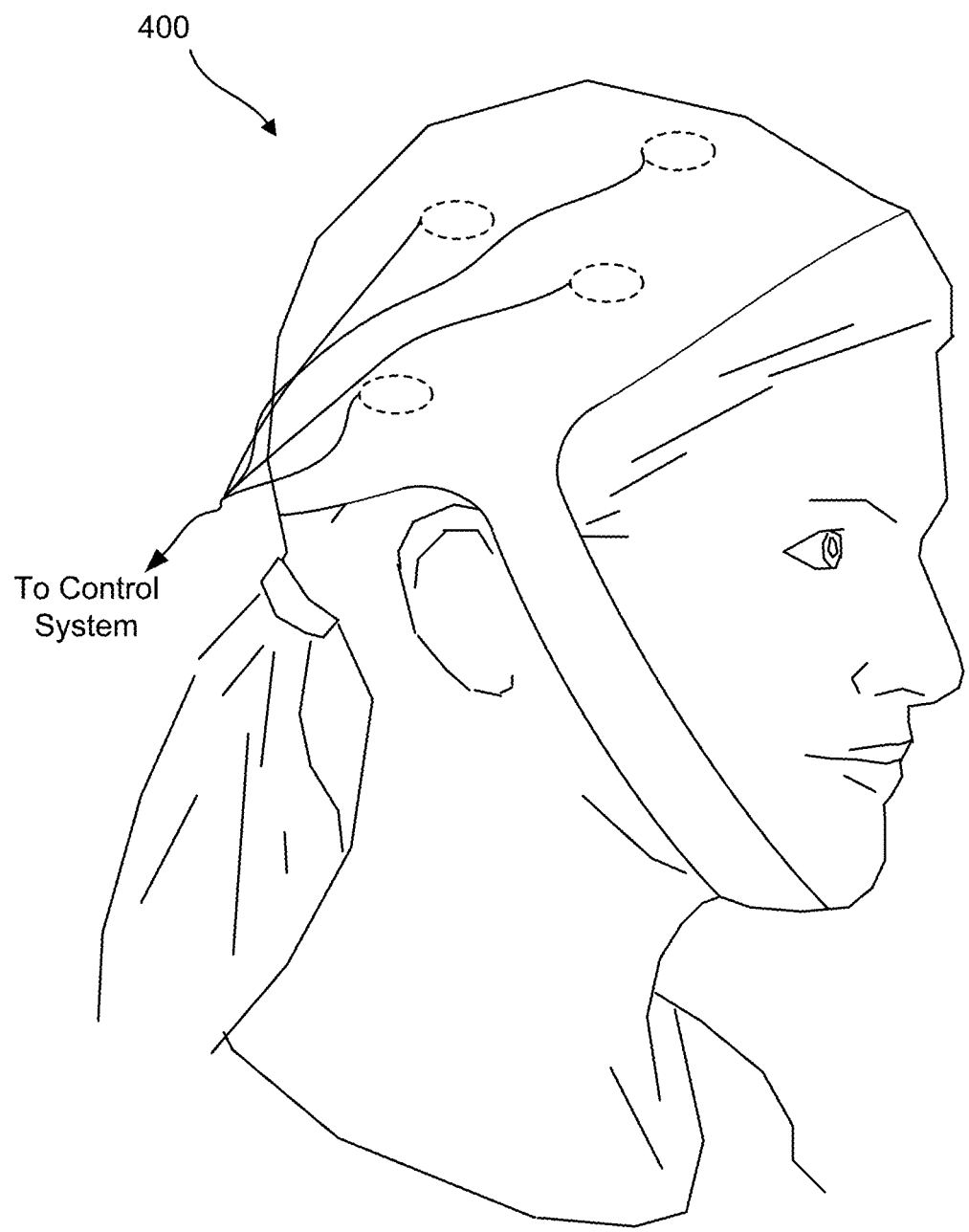
FIGS. 5A-5C depict Transcranial Electromagnetic Treatment (TEMT) to the human head, according to an example of the principles described herein.

FIG. 5A shows a subject wearing a TEMT device (400), which is an example of a method for providing Transcranial Electromagnetic Treatment (TEMT) to the head to treat brain cancers. An example of a TEMT device, called the OncosEM™, may be used to treat brain cancers. Electromagnetic waves are generated by the device with a combination control box/battery worn on the arm. A cable containing eight wires connects this control box/battery to each of the eight electromagnetic emitters (FIG. 4, 402) located within a double-layered head cap. The TEMT device (FIG. 5A, 400) permits near complete mobility in-home, allowing the wearer to perform most home activities while receiving electromagnetic treatment. The TEMT device (400) can be adjusted to several power levels, and emits no sound.

Figure 5B:
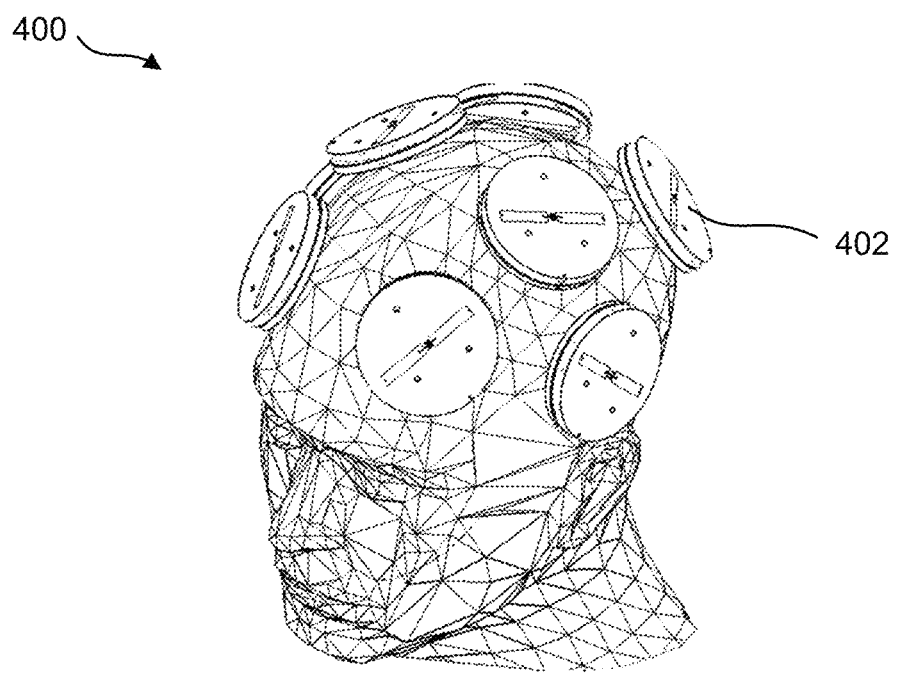

FIG. 5B depicts the size and location of the eight electromagnetic emitters (402) enveloped between the two-layer head cap. For simplicity, a single electromagnetic emitter (402) is indicated with a reference number. Sequential activation of these eight electromagnetic emitters (402) during any given treatment session allows for only one electromagnetic emitter (402) to be active at any given time, although simultaneous activation can also be accomplished.

Figure 5C:
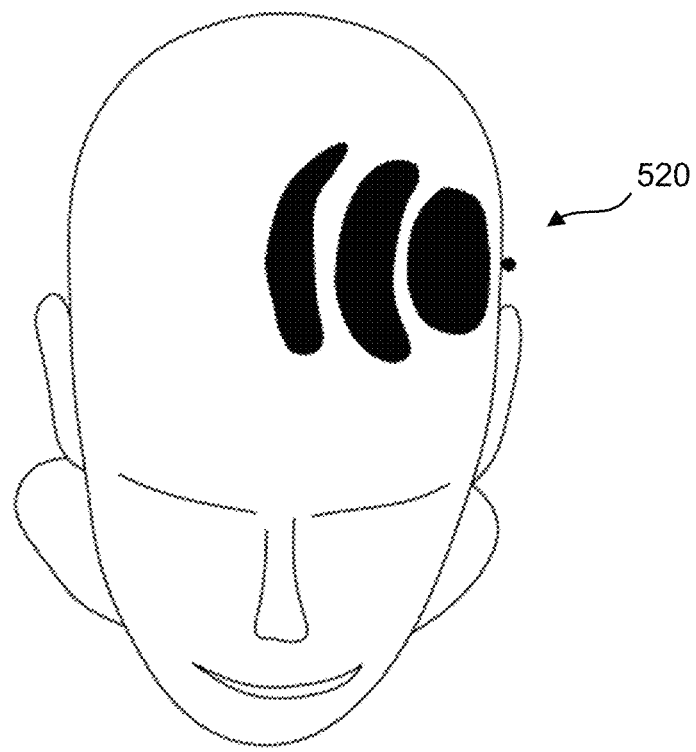

FIG. 5C depicts a finite-difference time-domain (FDTD) computer simulation (520) of the electric field generated by a single active electromagnetic emitter (402) set at 915 MHz frequency and 4.0 W/kg Specific Absorption Rate (SAR). Given the distribution and penetration depth of the electric field from this one active electromagnetic emitter (402) into the brain's temporal lobe, it can be appreciated that all eight electromagnetic emitters (402) during any given treatment provide for full forebrain electromagnetic field treatment. There may be around 200 treatment cycles (emitter activations) per second, but this "pulse repetition rate" can be lower (e.g., 40 Hz) or higher (e.g., 250 Hz).

As discussed above, MLVs are critical for drainage of brain intra-tumor fluid (containing memory T-cells and dendritic cells) to provide for a strong immune response to the tumor via memory T-cells generated in cervical lymph nodes that travel through the systemic circulation to the brain tumor site (e.g., as illustrated in FIGS. 1-3). As such, MLVs may serve as "tumor-associated lymphatics" linking the brain to peripheral immune responsivity.

Figure 6:
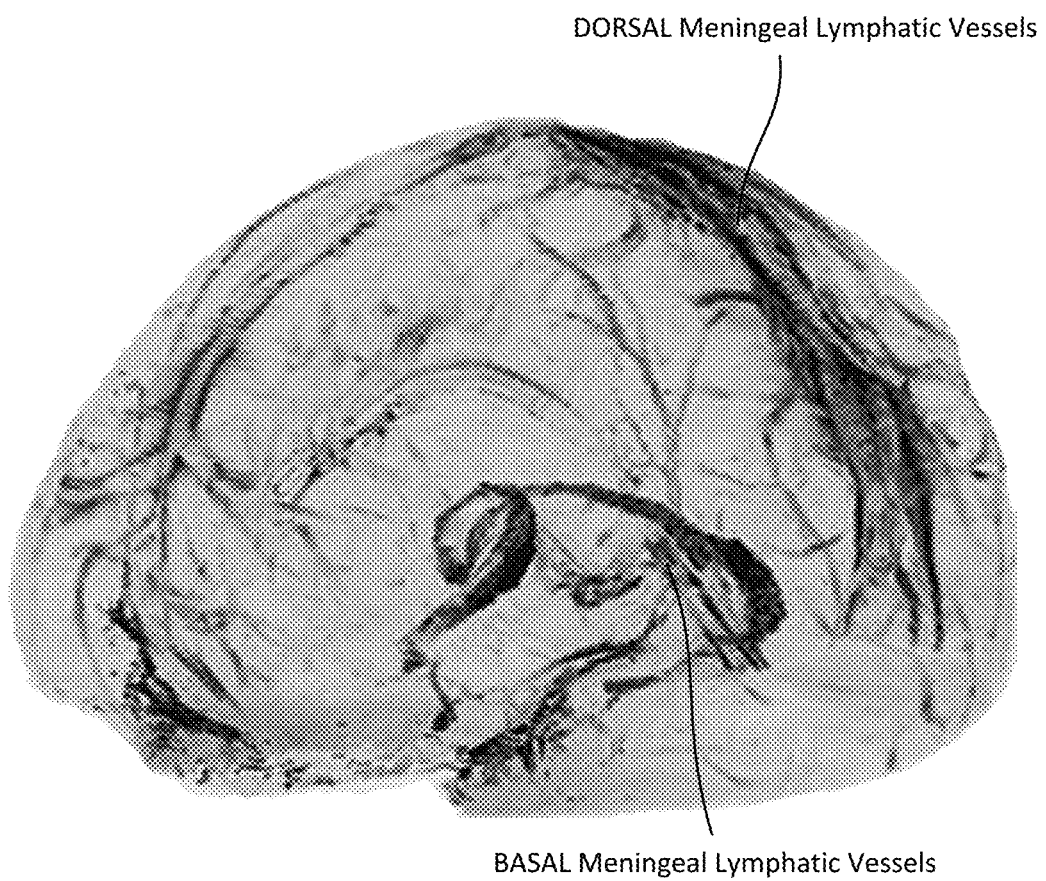
FIG. 6 shows the human brain's meningeal lymphatic vessels (MLVs), which are comprised of both "dorsal" and "basal" lymphatic vessel.

FIG. 6 shows the human brain's meningeal lymphatic vessels (MLVs), which are comprised of both "dorsal" and "basal" lymphatic vessel. There is evidence that dorsal MLVs are particularly important for transporting lymph containing memory T-cells and dendritic cells from the brain tumor to cervical lymph nodes, wherein an immune response to the tumor can be initiated. The dorsal MLVs, which directly drain CSF appear to be critical for draining intra-tumor fluid from solid brain cancers, while basal MLVs primarily serve as a sink for removal of toxins (including $A\beta$ and tau) from the brain. For both locations, methods to augment MLV function through MLV dilation or through a re-balancing of brain and/or blood cytokine/immune mediator levels may be highly desirable to treat brain cancers, with or without standard brain cancer treatments.

It has been very recently demonstrated that brain rejection of brain cancers (specifically gliomas) in rodents is facilitated by dilation of MLVs in rodents through experimental injection or viral delivery of the cytokine Vascular Endothelial Growth Factor (VEGF) into their CSF. Such VEGF treatment to expand MLVs induces a large increase in specific memory T-cells to the tumor location and rejection of the glioma cells. Thus, administration of VEGF into the CSF to dilate MLVs (dorsal ones in particular) could be a new therapeutic approach against brain cancers. However, direct administration of VEGF into the human brain's CSF or MLVs would be invasive, risky, and impractical on a long-term basis. Other methods are needed that are non-invasive and are effective long-term in modulating brain/CSF or blood levels of VEGF. Indeed, methods to modulate or rebalance brain/blood cytokine levels in general could provide an effective immune response to brain tumors to induce their rejection.

Figure 7:
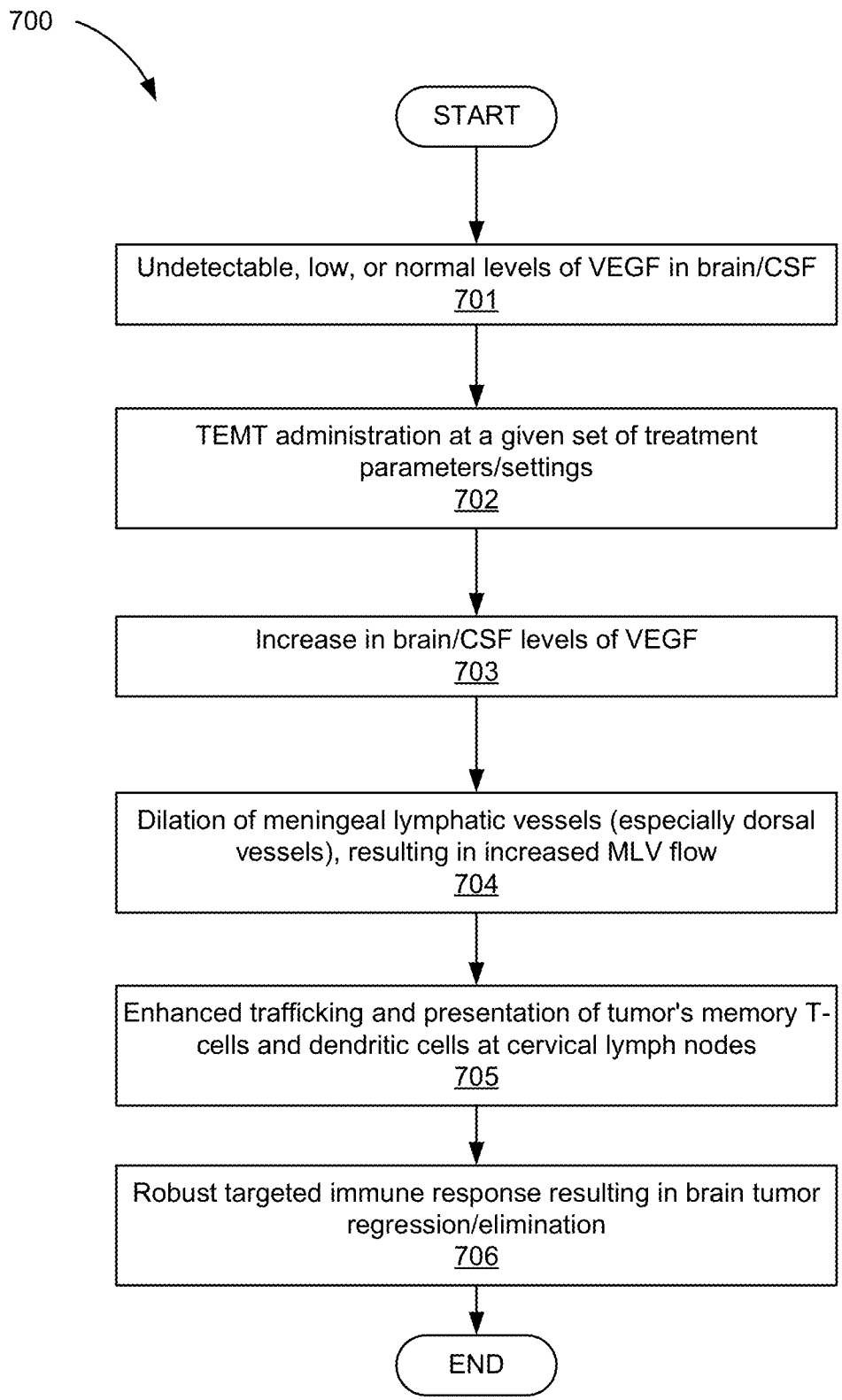
FIG. 7 is a flowchart of a first method for treatment of brain cancers with TEMT in which subjects would have undetectable, low, or normal baseline levels of the cytokine Vascular Endothelial Growth Factor (VEGF) in their brain/CSF and treatment would result in regression or elimination of the brain cancer.

In the current specification, methods for TEMT are presented that are novel and effective interventions to contain and cause eventual rejection of both primary and metastatic brain cancers. FIG. 7 is a flowchart of a first method (700)

for treatment of brain cancers with TEMT. In this first method, at (701), subjects would have undetectable, low, or normal baseline levels of the cytokine Vascular Endothelial Growth Factor (VEGF) in their brain/CSF. In subjects with undetectable, low, or normal VEGF levels in brain/CSF, at (702), TEMT may be administered at a given set of treatment parameters/settings. At (703), the TEMT administration may induce an increase in VEGF in brain/CSF that would cause, at (704) dilation of dorsal MLVs, resulting in increased lymph flow. At (705), enhanced trafficking and presentation of the tumor's memory T-cells and dendritic cells may occur at cervical lymph nodes. At (706), a robust targeted immune response resulting in brain tumor regression/elimination may occur.

Figure 8:
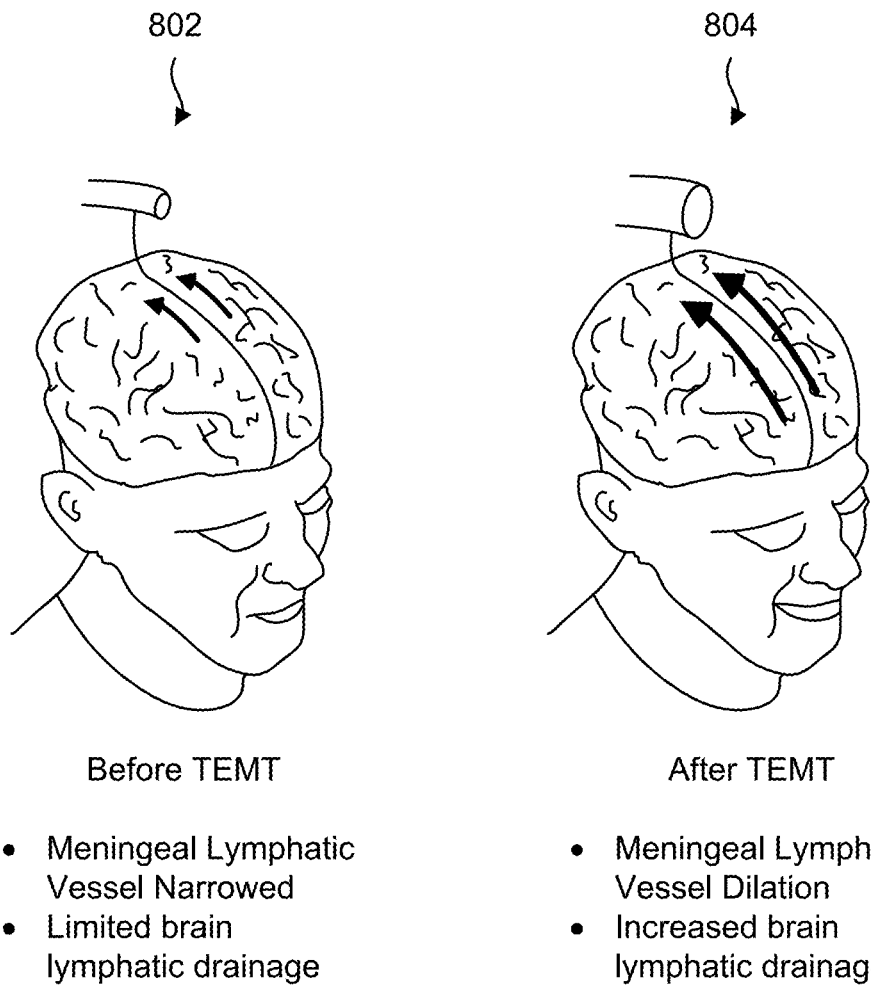
FIG. 8 depicts the brain's dorsal MLV vessels and their flow both before and after TEMT.

FIG. 8 depicts a subject's dorsal MLV flow both before (802) and after (804) TEMT. MLV flow is substantially increased following TEMT due to increased brain/CSF levels of VEGF. This increased VEGF dilates MLVs to facilitate transport of memory T-cells and dendritic cells from the tumor to cervical lymph nodes. At cervical nodes, an aggressive immune attack is mounted against the brain tumor via the blood. Thus, TEMT alone, or in combination with standard glioma treatments (e.g., anti-PD-1/CTLA-4), may result in glioma regression and the patient's remission.

Figure 9:
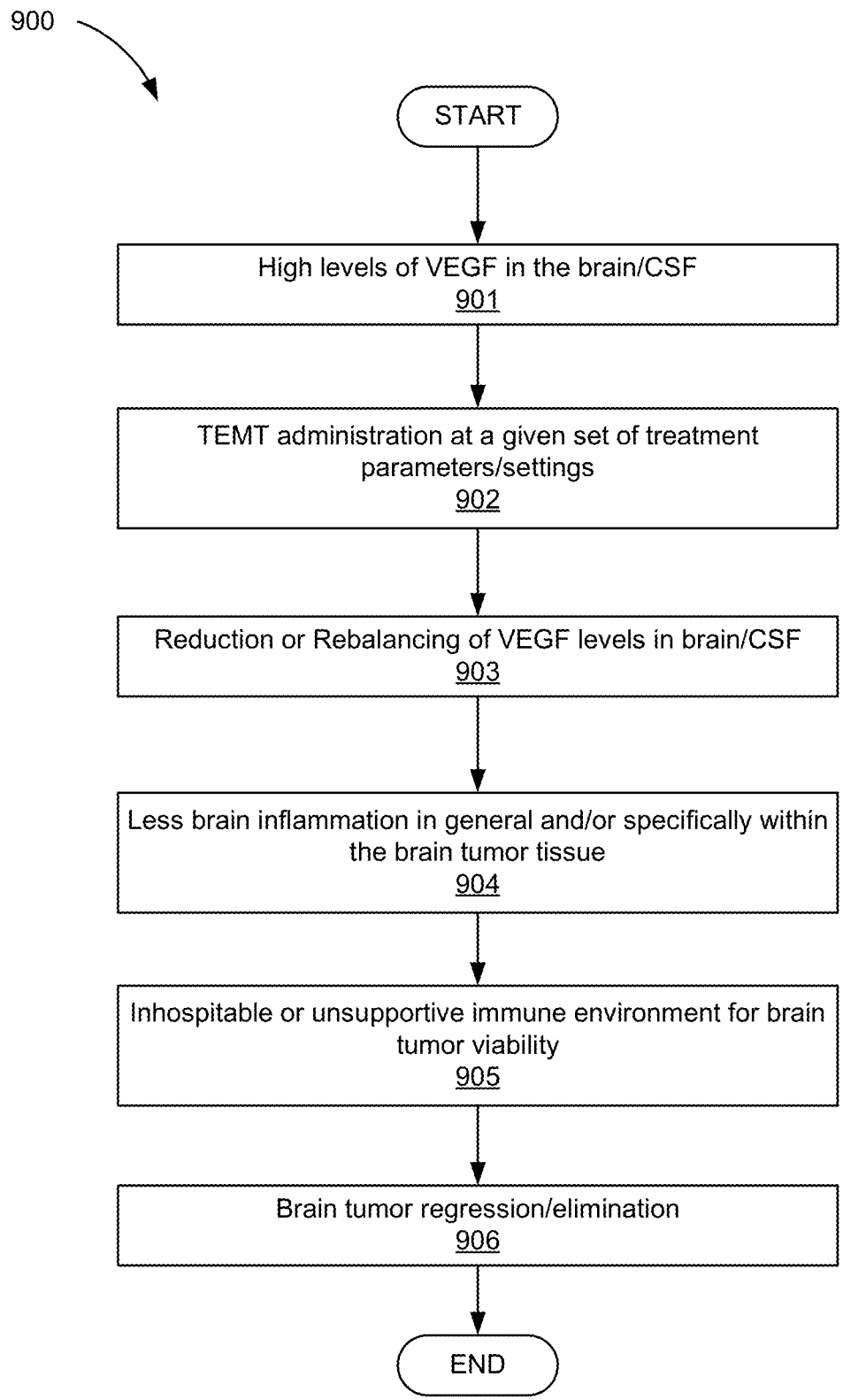
FIG. 9 is a flowchart of a second method for treatment of brain cancers with TEMT wherein subjects would have high levels of the cytokine VEGF in their brain/CSF and TEMT results in regression or elimination of the brain cancer.

FIG. 9 is a flowchart of a second method (900) for treatment of brain cancers with TEMT wherein subjects would have high levels of VEGF in their brain/CSF. In this case and according to the principles described herein, a cascade of events would occur to lower and/or "rebalance" VEGF levels in the brain. Brain tumors themselves can result in generalized brain inflammation. For example, 90% of glioma patients have been reported to have high VEGF levels in their CSF. Moreover, VEGF levels within certain brain tumors can be 200-300× higher than in plasma. As presented in FIG. 9, this second method aims to reduce or rebalance these high VEGF levels in brain, resulting in less overall brain inflammation and/or less inflammation within the tumor itself. Such a resulting inhospitable or unsupportive environment for tumor viability would then bring about in tumor regression or elimination.

At (901), high levels of VEGF in the brain/CSF may be present. At (902), TEMT administration may occur at a given set of treatment parameters/settings. At (903), reduction or rebalancing of VEGF levels in brain/CSF may occur in response to the TEMT administration. At (904), less brain inflammation in general and/or specifically within the brain tumor tissue may occur. At (905), inhospitable or unsupportive immune environment for brain tumor viability is generated. At (906), brain tumor regression or elimination may result from the inhospitable or unsupportive immune environment for the brain tumor.

Figure 10:
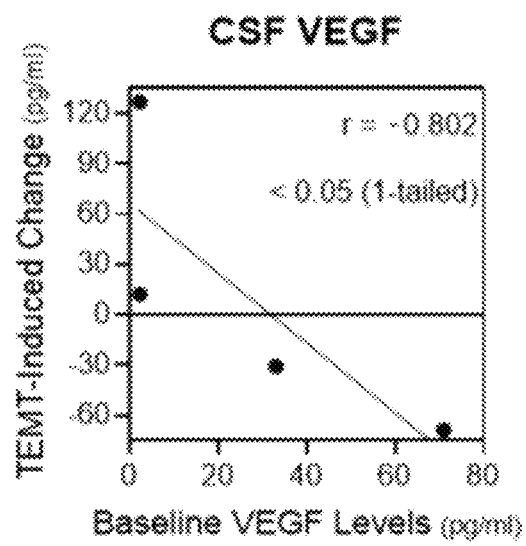
FIG. 10 is a graph displaying the immune normalizing/rebalancing ability of TEMT in the human brain by showing a significant inverse correlation between baseline levels of VEGF in brain/CSF vs. the TEMT-induced change in VEGF.

FIG. 10 presents direct clinical evidence for the stimulating/rebalancing effect of TEMT on brain/CSF levels of VEGF to induce beneficial effects against brain tumors. In humans with mild/moderate Alzheimer's Disease, a 2-month period of twice-daily TEMT reveals a clear immune-stimulation/rebalancing ability of TEMT. Specifically, if baseline VEGF levels in brain/CSF were low, TEMT induced a sizable increase in those levels, with just the opposite effect of TEMT if baseline VEGF levels were high. The significant inverse correlation between baseline VEGF levels and the direction/extent of TEMT-induced response ($r=-0.802$) clearly indicates a stimulation or rebalancing of VEGF in the human brain/CSF by TEMT.

Figure 11:
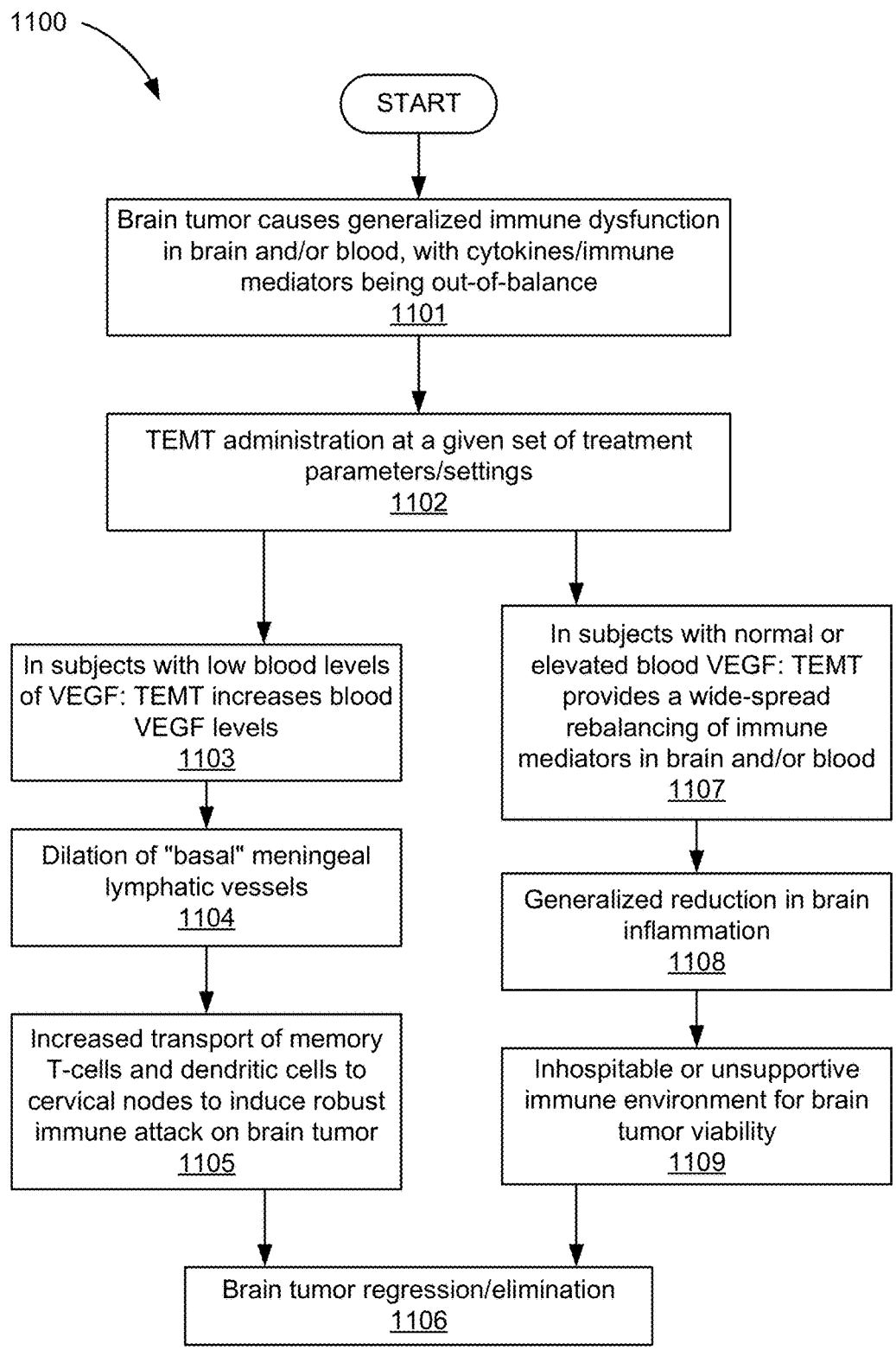
FIG. 11 is a flowchart of a third method for treating brain cancers with TEMT that involves TEMT providing a generalized rebalancing of multiple cytokines/immune mediators in both brain/CSF and blood, resulting in a regression or eliminate of the brain cancer.

FIG. 11 presents a flowchart showing yet another method (1100) of TEMT action against brain cancers, wherein VEGF levels in the brain/CSF or blood can be high or low.

At (1101), a brain tumor may cause generalized immune dysfunction in brain and/or blood. For example, cytokines/immune mediators may be out of balance. This third method involves, at (1102), TEMT providing a generalized rebalancing of multiple cytokines/immune mediators in both brain/CSF and blood by TEMT. It is very possible that presence of the brain cancer (especially with metastasis to the brain from other tissues) has resulted in the brain and immune system being very much out of balance (i.e., cytokine/immune mediator levels being either too high or too low in brain or blood).

This third method could be particularly beneficial to subjects with low "blood" levels of VEGF. At (1103), TEMT may increase blood VEGF levels and, in so doing, at (1104), dilate "basal" MLVs. Such a dilation of MLVs would, at (1105), facilitate transit of memory T-cells and dendritic cells from the tumor fluid to elicit an immune activation at cervical lymph nodes, as previously described. At (1106), brain tumor regression or elimination may result.

Alternatively, or in addition, TEMT could be providing a rebalancing of cytokines levels in brain/CSF and blood in general to facilitate regression of primary tumors in the brain or of metastatic cancers throughout the body that have spread to the brain. At (1107), in subjects with normal or elevated blood VEGF, TEMT may provide a wide-spread rebalancing of immune mediators in the brain and/or blood. At (1108), a generalized reduction in brain inflammation may occur in response to the TEMT treatment. At (1109), inhospitable or unsupportive immune environment for brain tumor viability is generated. At (1106), brain tumor regression or elimination may result.

Figure 12:
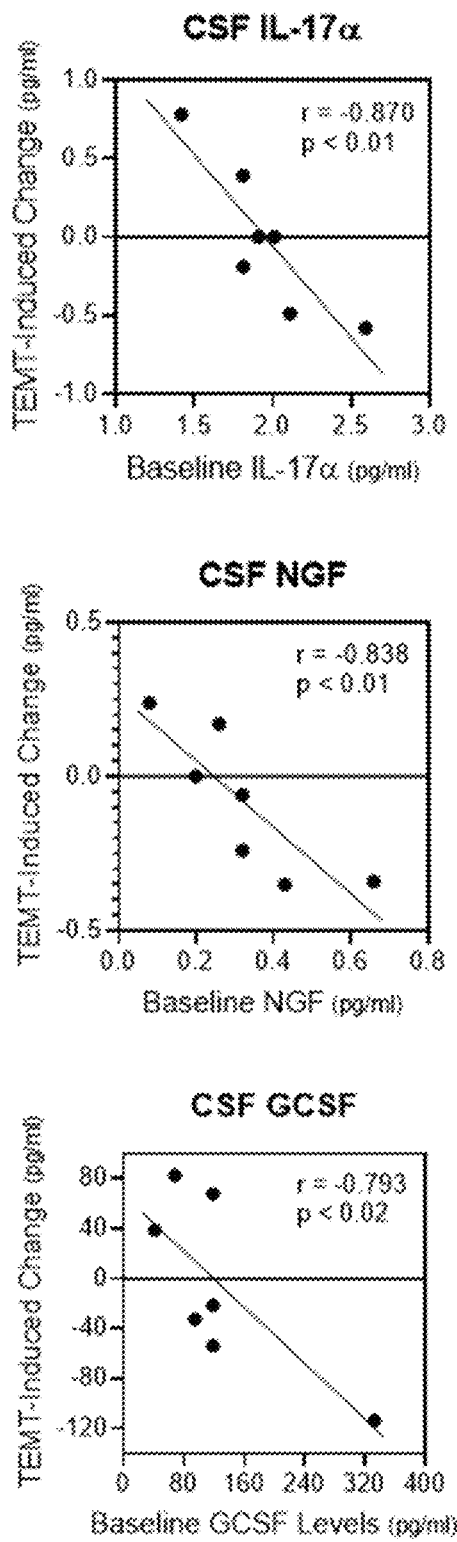
FIG. 12 presents three graphs displaying the immune normalizing/rebalancing ability of TEMT in the human brain by showing significant inverse correlations between baseline levels of IL-17α, NGF, and GCSF in brain/CSF vs. TEMT-induced change in these cytokines/immune mediators.

FIG. 12 presents direct clinical evidence for the normalizing/rebalancing effect of TEMT on brain/CSF levels of various cytokines/immune mediators. In humans with mild/moderate Alzheimer's Disease, a 2-month period of twice-daily TEMT provides a clear immune normalizing/rebalancing ability of TEMT, as demonstrated graphically in FIG. 12 for three cytokines in brain/CSF—IL-17α, NGF, and GCSF. Specifically, if baseline cytokine levels were low, 2 months of TEMT resulted in elevated cytokine levels. Conversely, if brain/CSF cytokine levels were high, TEMT induced a reduction in their levels. For these and several other cytokines in brain/CSF, highly significant correlations were present in that baseline levels of CSF cytokines determined the direction and extent of their response to TEMT—this is clearly an immune normalizing/rebalancing action of TEMT in the brain that could be critically important for therapeutic intervention against brain cancers.

Figure 13:
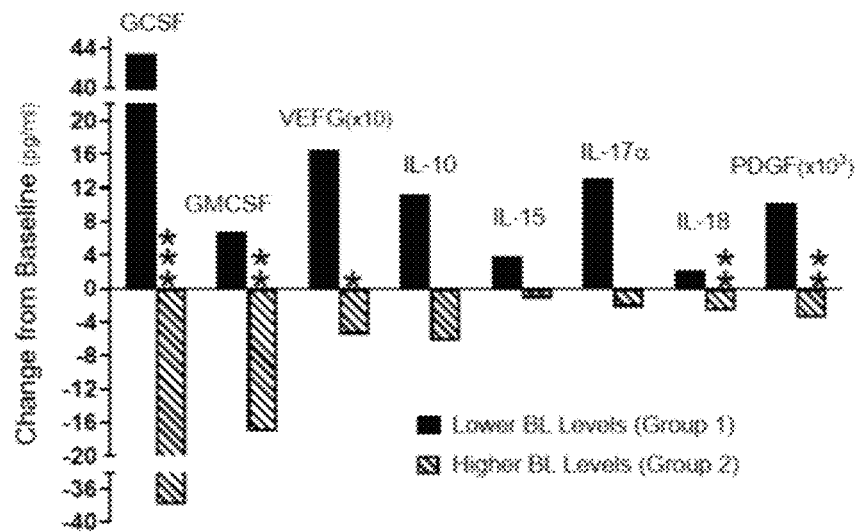
FIG. 13 shows the profound normalizing/rebalancing effect of TEMT on blood levels of eight cytokines in humans.

FIG. 13 presents direct clinical evidence for TEMT providing extensive rebalancing of the immune system in blood by showing the direction and extent of changes in levels of eight cytokines/immune mediators induced by two-months of daily TEMT. When comparing Group 1 (lower baseline levels) to Group 2 (higher baseline levels), the direction of response to TEMT for all eight cytokines is universally opposite for these two groups. For all eight cytokines in blood and all subjects individually and collectively, if initial blood levels of these cytokines were below normal, TEMT increased those levels to normal or near normal levels. If initial blood levels of these eight cytokines were above normal, TEMT decreased those levels to normal or near normal levels. This profound normalizing/rebalancing effect of TEMT on blood cytokine levels was not only present after 2-months of daily TEMT administration, but it was even present after a single 1-hour treatment with TEMT (as illustrated in FIG. 14).

Figure 14:
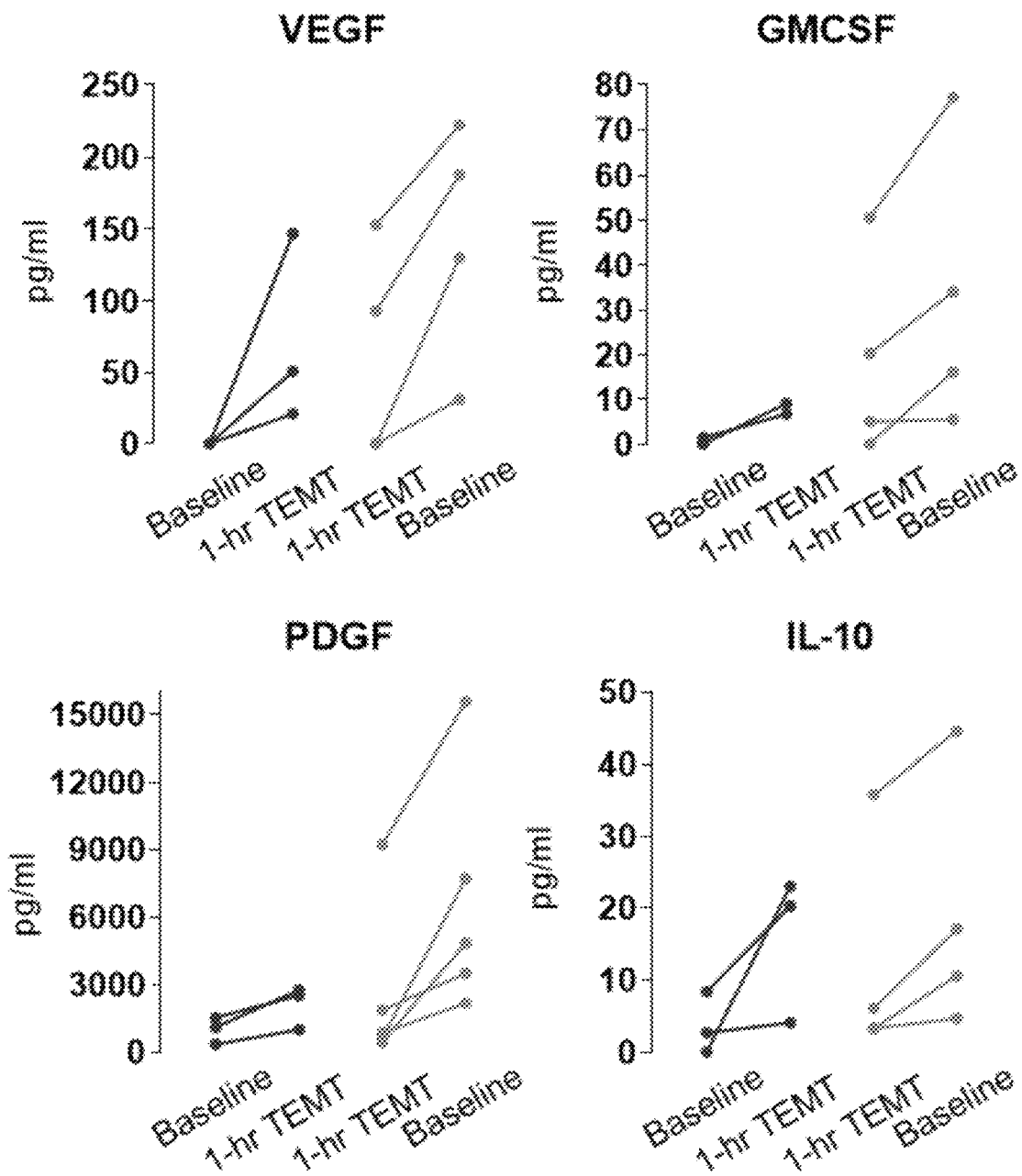
FIG. 14 presents the effects of a single 1-hour TEMT treatment on plasma levels of four cytokines in human subjects. For all four cytokines, if baseline blood levels were low (black symbols and lines), 1-hour of TEMT increased levels, with just the opposite effect of TEMT if baseline blood levels were high (gray symbols and lines).

FIG. 14 presents the effects of a single 1-hour TEMT treatment on plasma levels of four cytokines in human subjects. For all four cytokines, if baseline blood levels were low (black symbols and lines), 1-hour of TEMT increased levels, with just the opposite effect of TEMT if baseline blood levels were high (gray symbols and lines). The clinical results shown in FIGS. 13 and 14 indicate that TEMT induces both chronic and acute rebalancing effects on blood cytokines/immune markers that are essentially the same in direction and extent.

Figure 15:
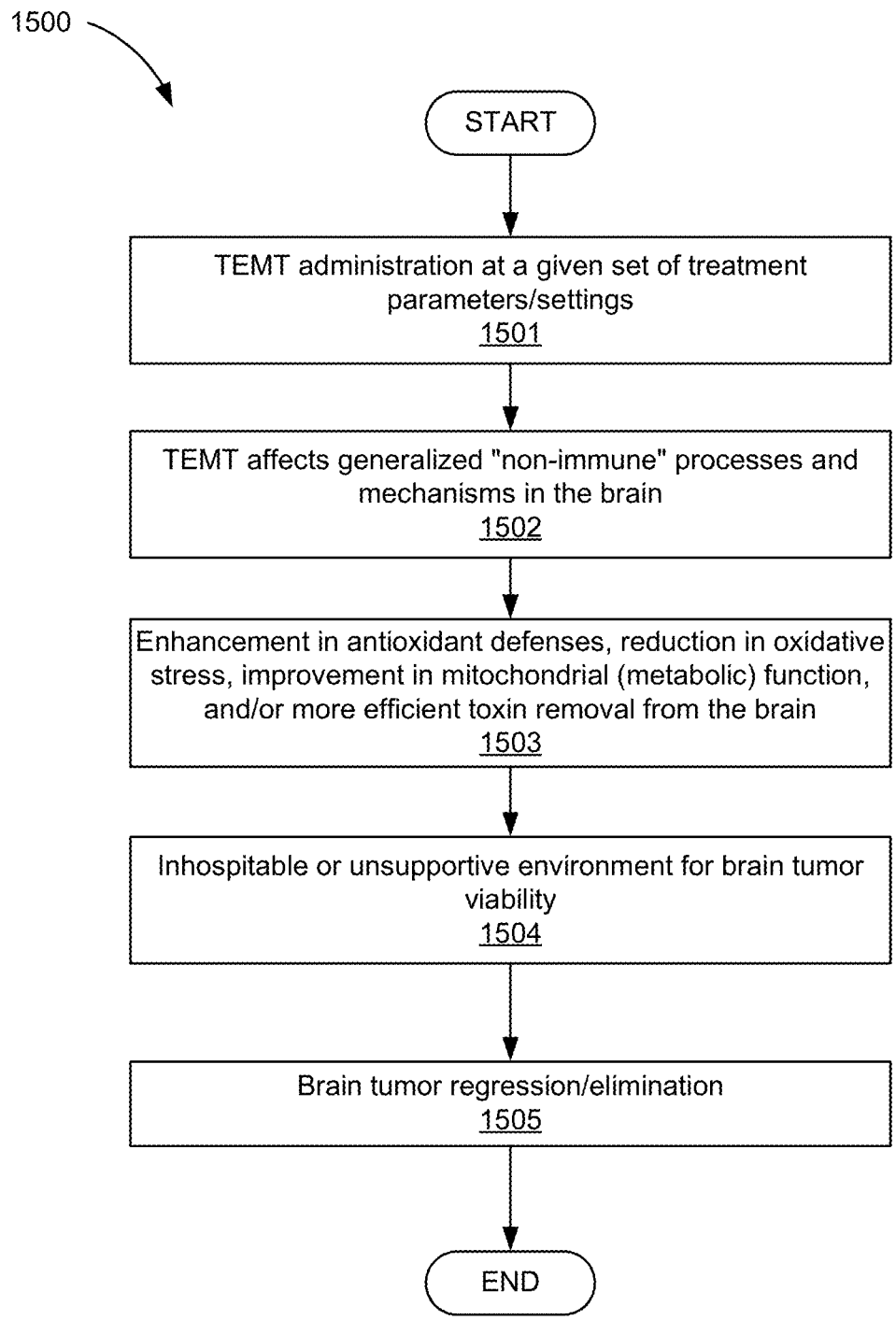
FIG. 15 is a flowchart of a fourth method for TEMT treating brain cancers whereby TEMT provides anti-tumor actions by affecting generalized non-immune processes in the brain, resulting in brain tumor regression or elimination.

FIG. 15 is a flowchart of a fourth method (1500) for TEMT treating brain cancers whereby TEMT provides anti-tumor actions by affecting generalized "non-immune" processes in the brain, resulting in brain tumor regression or elimination. This fourth method (1500) for TEMT to treat brain cancers involves TEMT providing anti-tumor actions not through generalized immune actions (e.g., the third method (1100), but by affecting generalized "non-immune" processes in the brain. These additional actions by TEMT are depicted in the flowchart of FIG. 15 and include, but are not limited to, potential enhancement in antioxidant defenses, reductions in oxidative stress, increased mitochondrial (metabolic) function and/or more efficient toxin removal from the brain. Any of these and/or other potential non-immune benefits of TEMT, could result in an inhospitable or unsupportive environment for brain tumor viability, leading to tumor regression or elimination.

At (1501), TEMT may be administered at a given set of treatment parameters/settings. At (1502), TEMT may affect generalized non-immune processes and mechanisms in the brain. At (1503), enhancement in antioxidant defenses, reduction in oxidative stress, improvement in mitochondrial (metabolic) function, and/or more efficient toxin removal from the brain may occur. At (1504), inhospitable or unsupportive immune environment for brain tumor viability is generated. At (1505), brain tumor regression or elimination may result from the inhospitable or unsupportive immune environment for the brain tumor.

Figure 16:
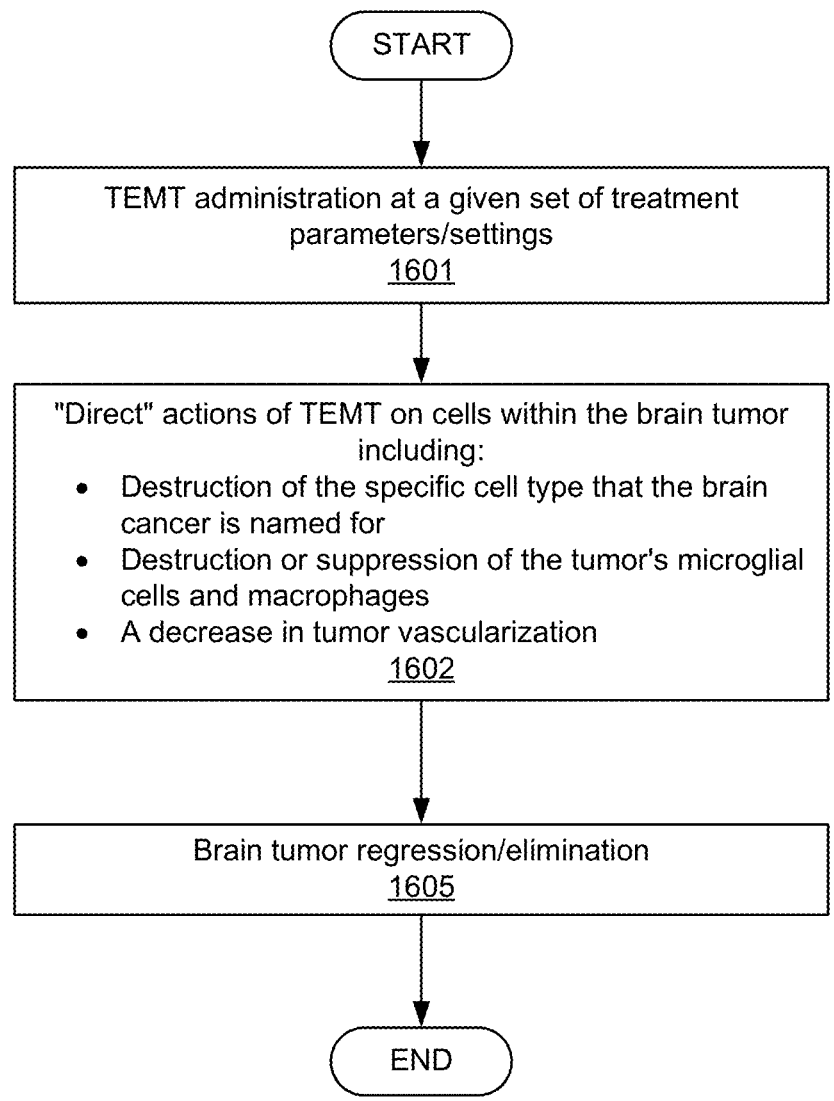
FIG. 16 is a flowchart of a fifth method for TEMT treating brain cancers whereby TEMT provides anti-tumor actions directly within the brain tumor(s), resulting in brain tumor regression or elimination.

FIG. 16 is a flowchart of a fifth method (1600) for TEMT treating brain cancers whereby TEMT provides anti-tumor actions directly within the brain tumor(s), resulting in brain tumor regression or elimination. The fifth method (1600) for TEMT treating brain cancers involves TEMT providing anti-tumor actions directly within the brain tumor(s), as shown in the flowchart in FIG. 16. For this method (1600), levels of cytokines or immune mediators in brain/blood may not be relevant because the action of TEMT is directly on cells within the tumor itself. In addition to the cancerous cell type that gives a given brain cancer its name (e.g., astrocytoma), other cell types reside within many brain tumors include endothelial cells, mesenchymal stem cells, microglia, and macrophages. Regarding the last of these cell types, microglia and macrophages constitute up to 30% of a glioma's mass and can cause either immunosuppression or inflammation within the tumor. A method to destroy or reduce the activity of these microglia and macrophage cell types within a given brain tumor would be highly desirable. In that regard, direct actions of TEMT (1601) on tumor cells and/or their immediate surrounds may cause (at 1602): 1) destruction of the specific cell type that the brain cancer is named for, 2) destruction or suppression of the tumor's microglial cells/macrophages, and/or 3) a decrease in tumor vascularization. At (1603), brain tumor regression or elimination may result.

Activated microglia within brain tumors adopt a pro-inflammatory profile, releasing various inflammatory cytokines. An ability of TEMT to destroy, deactivate, or suppress such microglia within brain tumors may be highly advantageous for causing regression or atrophy of brain tumors. Along that line, previous studies have reported radiofrequency wave effects at 900-915 MHz on "normal" brain microglial cells (not within brain tumors), suggesting that a direct effect of TEMT on microglial cells to decrease inflammation within the brain tumor is possible and perhaps likely.

Regarding gliomas in particular, it may be the case that they have uncontrolled microglia-based inflammation/cytokine levels, which may be responsible for at least some of the glioma growth from mild to moderate to severe stages. However, just the opposite may be the case for the MLVs, wherein low cytokines are present (most importantly VEGF) and an enhanced VEGF presence is needed to dilate MLFs or otherwise facilitate transport of tumor-based fluid/cells to cervical lymph nodes. Here, the brain/CSF levels of VEGF are too low, with the resulting inability of limited MLV lymph flow to trigger a vigorous immune response. In either case, the present methods regulate brain/CSF cytokine levels, which may include reducing brain inflammation in the tumor and up-regulating cytokine levels in CSF and the MLVs. Such a method could be extraordinarily therapeutic against many types of brain cancers.

For all of the above methods to address brain tumor treatment and other applications of TEMT related to such treatment, the following ranges of electromagnetic/radiofrequency wave parameters being emitted may be used:
 a. an electromagnetic wave frequency of 1 MHz to 430 GHz
 b. a power level of 0.1 to 16 W/kg average Specific Absorption Rate (SAR)
 c. a pulse repetition rate of 1 to 300 Hz
 d. a duty cycle between 1% and 100% (continuous).

In addition, for all of the above methods to address brain tumor treatment, any given treatment session may have a specified duration of for example a few minutes to a few hours, or it may be continuous over days, weeks, months, or years. Any given treatment session may be repeated at predetermined intervals, for example for multiple times a week, etc. over a longer period of time such as a month or even years.

For the described methods, variations from their general methods may be included, which may include but are not limited to:
 a methodologic variation whereby the brain tumor(s) is/are targeted directly with one or several emitters aimed directly at the tumor(s) and activated either sequential or simultaneously. Global TEMT (all eight emitters active) may be a first methodologic approach to treat the entire forebrain followed by, or in conjunction with, treatment to specific tumor-containing areas of the brain; and
 a methodologic variation whereby higher TEMT power levels may be needed for deep sub-cortical brain tumors, such as those in the brain stem or near the optic nerve. With most gliomas being located in one of the four cerebral lobes, however, lower power settings of the OncosEM™ device may be appropriate, at least initially.

Figure 17A:
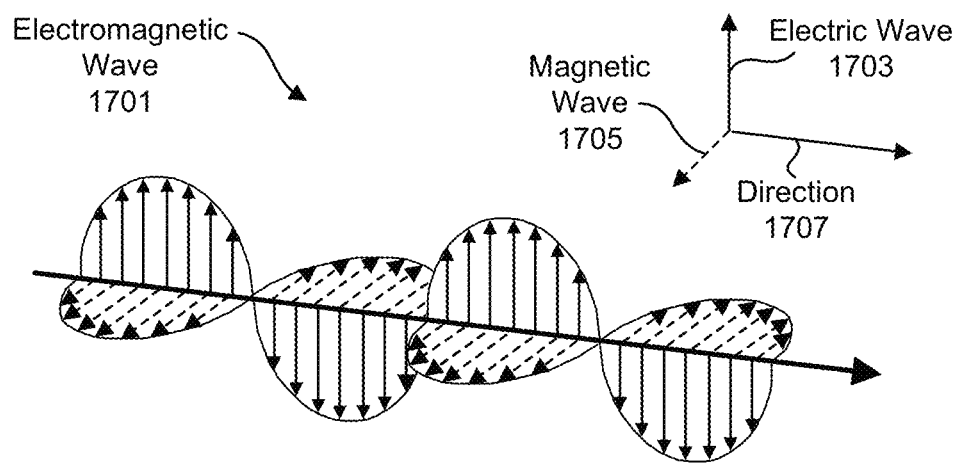
FIGS. 17A and 17B show differences between TEMT's true electromagnetic waves consisting of interdigitated electric and magnetic waves, and magnetic waves generated by magnets.
Figure 17B:
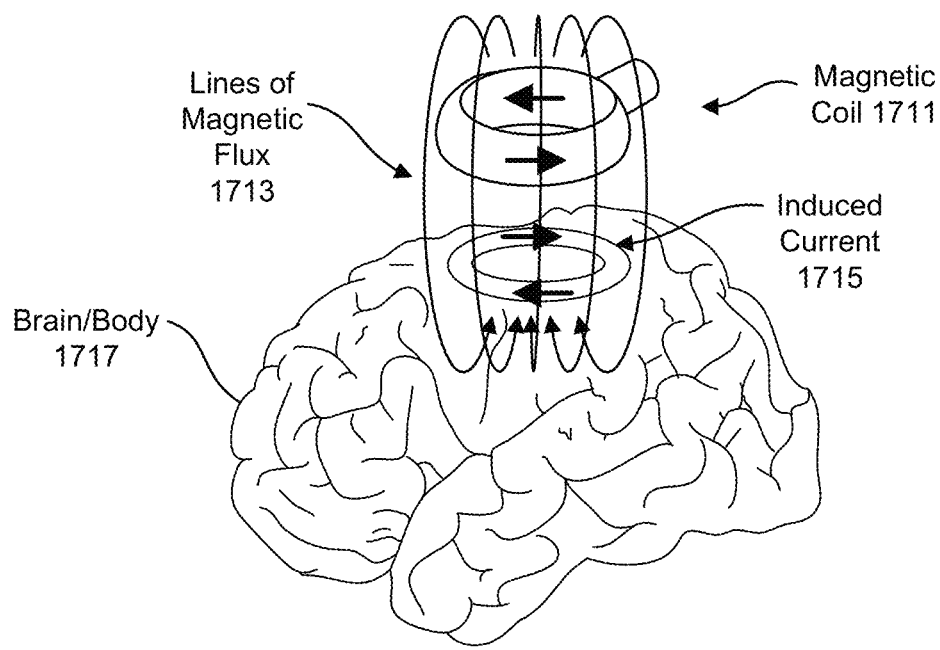

As used in the present specification and in the appended claims, the term "electromagnetic fields" or "electromagnetic treatment" refer to interdigitated electric and magnetic waves generated by an electromagnetic wave generator, sent to an emitter and then passed into tissue as electromagnetic fields/treatment (FIG. 17A). These are "true" electromagnetic waves which should not be confused with the completely different modality of "magnetic stimulation/treatment", which involves generation of magnetic waves by magnets, with ensuing induction of completely separate electric waves in the tissue at a right angle to the magnetic waves on the tissue surface (FIG. 17B). Such magnetic stimulation is often, but erroneously, referred to as "electromagnetic stimulation, electromagnetic waves, Pulsed Electromagnetic Fields (PEMF's) or Extremely Low Frequency EMF (ELF-EMF)". Knowing what is truly electromagnetic treatment (interdigitated electric and magnetic waves) can be determined by looking at the units of power—true electromagnetic waves (FIG. 17A) use W/kg or Specific Absorption Rate (SAR), while the above magnetic waves/stimulations (FIG. 17B) use "tesla" magnetic units.

FIG. 17A illustrates an example of TEMT electromagnetic waves (1701) having interdigitated electric waves (1703) and magnetic waves (1705) moving in a given direction (1707).

FIG. 17B illustrates an example of magnetic waves generated by magnets, such as in magnetic stimulation of a tissue. In this case, the magnetic waves generated by magnets are often referred to erroneously as electromagnetic waves or pulsed electromagnetic treatment (PEMT). In this example, a magnetic coil (1711) generates a magnetic flux (1713), which induces a current (1715) in the brain/body (1717). It should be noted that the present specification is not referring to "magnetic stimulation/treatment", which involves generation of magnetic waves (e.g., magnetic flux (1713) into a tissue by magnets, with ensuing induction of completely separate electric waves at a right angle to the magnetic waves in the tissue.

The preceding description has been presented only to illustrate and describe the invention. It is not intended to be exhaustive or to limit the invention to any precise form disclosed. Many modifications and variations are possible in light of the above teaching.

The examples described herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. A method for treating gliomas and other primary tumors in the brain of a subject, the gliomas and other primary tumors including glioblastomas, astrocytomas, oligodendrogliomas, oligoastrocytomas, chordomas, ependymomas, schwannomas and pituitary tumors; the method comprising:
    positioning one or an array of electromagnetic emitters of a non-thermal transcranial electromagnetic treatment (TEMT) device proximal to a head of a subject;
    generating, by an electromagnetic wave generator, electromagnetic fields having predetermined treatment parameters; and
    causing regression or elimination of the glioma in an area under the electromagnetic emitters by applying the electromagnetic field to the subject through the electromagnetic emitters.

2. The method of claim 1, in which the subject has undetectable, low, or normal baseline levels of the cytokine VEGF in their brain/CSF and treatment results in increased VEGF levels in brain/CSF to increase lymph flow in meningeal lymphatic vessels, thus inducing an immune response for brain tumor regression or elimination.

3. The method of claim 1, wherein the subject has undetectable, low, or normal blood levels of VEGF and TEMT induces increased basal meningeal lymphatic flow to increase trafficking of tumor constituents to cervical lymph nodes triggering a robust immune response against the brain tumor.

4. The method of claim 1, in which the subject has high baseline levels of the cytokine VEGF in their brain/CSF and treatment results in rebalancing of VEGF levels in brain/CSF to induce less brain inflammation and an unsupportive environment for tumor survival.

5. The method of claim 1, wherein TEMT provides a wide-spread rebalancing of immune mediators in brain and blood to reduce brain inflammation in general, resulting in an inhospitable or unsupportive immune environment for tumor viability.

6. The method of claim 1, wherein TEMT favorably affects generalized non-immune processes and mechanisms in the brain, which creates an inhospitable or unsupportive environment for brain tumor viability.

7. The method of claim 1, wherein TEMT directly acts on cells within the tumor by destruction of glioma cells, destruction or suppression of the tumor's microglial cells/macrophages, and/or a decrease in tumor vascularization.

8. The method of claim 1, wherein the area under the electromagnetic emitters comprises at least one of a glioma, neurons, normal brain glial, meningeal lymphatic vessels, and cerebral blood vessels.

9. The method of claim 1, wherein the electromagnetic waves have:
    a frequency of 1 megahertz (MHz) to 430 gigahertz (GHz);
    a power level of 0.1 to 16 watts per kilogram (W/kg) average Specific Absorption Rate (SAR);
    a pulse repetition rate of 1 to 300 hertz (Hz); and
    a duty cycle between 1% and 100%.

10. The method of claim 1, wherein glioma treatment with TEMT involves applying electromagnetic treatment to the subject through the electromagnetic emitters in periodic treatments at predetermined intervals.

11. The method of claim 1, wherein the non-thermal TEMT device causes regression or elimination of the glioma without irradiating the glioma.

12. A method for treating a metastasized brain tumor within a brain of a subject, the metastasized brain tumor comprising a lung cancer, a breast cancer, a lymphoma; the method comprising:
    positioning one or an array of electromagnetic emitters of a non-thermal transcranial electromagnetic treatment (TEMT) device proximal to a head of a subject;
    generating, by an electromagnetic wave generator, electromagnetic fields having predetermined treatment parameters; and
    causing regression or elimination of the metastasized brain tumor in an area under the electromagnetic emitters by applying the electromagnetic field to the subject through the electromagnetic emitters.

13. The method of claim 12, in which the subject has undetectable, low, or normal baseline levels of the cytokine VEGF in their brain/CSF and treatment would result in increased VEGF levels in brain/CSF to increase lymph flow in meningeal lymphatic vessels, thus inducing an immune response for brain tumor regression or elimination.

14. The method of claim 12, wherein the subject has undetectable, low, or normal blood levels of VEGF and TEMT induces increased basal meningeal lymphatic flow to increase trafficking of tumor constituents to cervical lymph nodes triggering a robust immune response against the brain tumor.

15. The method of claim 12, in which the subject has have high baseline levels of the cytokine VEGF in their brain/CSF and treatment would result in rebalancing of VEGF levels in brain/CSF to induce less brain inflammation and an unsupportive environment for tumor survival.

16. The method of claim 12, wherein TEMT provides a wide-spread rebalancing of immune mediators in brain and blood to reduce brain inflammation in general, resulting in an inhospitable or unsupportive immune environment for tumor viability.

17. The method of claim 12, wherein TEMT favorably affects generalized non-immune processes and mechanisms in the brain, which creates an inhospitable or unsupportive environment for brain tumor viability.

18. The method of claim 12, wherein TEMT directly acts on cells within the tumor by destruction of metastatic tumor cells, destruction or suppression of the metastasized brain tumor's microglial cells/macrophages, and/or a decrease in tumor vascularization.

19. The method of claim 12, wherein the area under the electromagnetic emitters comprises at least one metastatic brain tumor, neurons, normal brain glial, meningeal lymphatic vessels, and cerebral blood vessels.

20. The method of claim 12, wherein the electromagnetic waves have:
- a frequency of 1 megahertz (MHz) to 430 gigahertz (GHz);
- a power level of 0.1 to 16 watts per kilogram (W/kg) average Specific Absorption Rate (SAR);
- a pulse repetition rate of 1 to 300 hertz (Hz); and
- a duty cycle between 1% and 100%.

21. The method of claim 12, wherein glioma treatment with TEMT involves applying electromagnetic treatment to the subject through the electromagnetic emitters in periodic treatments at predetermined intervals.

\* \* \* \* \*